US007867218B1

(12) United States Patent
Voda

(10) Patent No.: US 7,867,218 B1
(45) Date of Patent: Jan. 11, 2011

(54) STEERABLE CATHETER FOR RIGHT CORONARY ARTERY

(75) Inventor: Jan K. Voda, Oklahoma City, OK (US)

(73) Assignee: Voda Heart Technology, LLC, Oklahoma City, OK (US)

( * ) Notice: Subject to any disclaimer, the term of this patent is extended or adjusted under 35 U.S.C. 154(b) by 984 days.

(21) Appl. No.: 10/786,893

(22) Filed: Feb. 24, 2004

(51) Int. Cl.
*A61M 25/00* (2006.01)
*A61M 5/00* (2006.01)
(52) U.S. Cl. .................. 604/532; 604/530; 604/264
(58) Field of Classification Search .................. 604/19, 604/48, 93.01, 264, 532, 530, 523, 528
See application file for complete search history.

(56) References Cited

U.S. PATENT DOCUMENTS

| | | |
|---|---|---|
| 3,935,857 A | 2/1976 | Co |
| 3,938,501 A | 2/1976 | Erikson |
| 4,020,829 A | 5/1977 | Willson et al. |
| 4,033,331 A | 7/1977 | Guss et al. |
| 4,117,836 A | 10/1978 | Erikson |
| 4,169,464 A | 10/1979 | Obrez |
| 4,195,637 A | 4/1980 | Grüntzig et al. |
| 4,292,976 A | 10/1981 | Banka |
| 4,430,083 A | 2/1984 | Ganz et al. |
| 4,547,193 A | 10/1985 | Rydell |
| 4,551,292 A | 11/1985 | Fletcher et al. |
| 4,563,181 A | 1/1986 | Wijayarathna et al. |
| 4,568,338 A | 2/1986 | Todd |
| 4,581,017 A | 4/1986 | Sahota |
| 4,582,181 A | 4/1986 | Samson |
| 4,616,653 A | 10/1986 | Samson et al. |
| 4,733,669 A | 3/1988 | Segal |
| 4,738,667 A | 4/1988 | Galloway |

(Continued)

FOREIGN PATENT DOCUMENTS

EP   0 132 344 A2   1/1985

(Continued)

OTHER PUBLICATIONS

Wiseguide™ ART3.0 guide catheter, SciMed Life Systems, Inc., Maple Grove, Minnesota (2 sheets) (undated but admitted to be prior art); U. S. Patent No. 5,674,208 issued Oct. 7, 1997 to Berg et al.

(Continued)

*Primary Examiner*—Nicholas D Lucchesi
*Assistant Examiner*—Victoria P Campbell
(74) *Attorney, Agent, or Firm*—Seager, Tufte & Wickhem, LLC

(57) ABSTRACT

A steerable three dimensional catheter to engage the ostium of a right coronary artery in a patient includes: a torque-transmitting proximal shaft that receives manipulation by a user outside a patient in whom the catheter is used; and a distal shaft that is responsive to torque transmitted by the proximal shaft. The distal shaft includes a preformed support section having at least a segment that abuts a posterior or left lateral interior surface of the ascending aorta of the patient. The distal shaft also includes a preformed ostium entry section extending from the support section. In one implementation, the ostium entry section transitions from the support segment abutting the aortic wall to a distal tip end by way of at least two differently directed angles.

12 Claims, 2 Drawing Sheets

U.S. PATENT DOCUMENTS

| | | | |
|---|---|---|---|
| 4,747,840 A | 5/1988 | Ladika et al. | |
| 4,748,982 A | 6/1988 | Horzewski et al. | |
| 4,762,129 A | 8/1988 | Bonzel | |
| 4,771,777 A | 9/1988 | Horzewski et al. | |
| 4,781,682 A | 11/1988 | Patel | |
| 4,784,639 A | 11/1988 | Patel | |
| 4,790,831 A | 12/1988 | Skribiski | |
| 4,813,930 A | 3/1989 | Elliott | |
| 4,820,349 A | 4/1989 | Saab | |
| 4,822,345 A | 4/1989 | Danforth | |
| 4,867,174 A | 9/1989 | Skribiski | |
| 4,877,031 A | 10/1989 | Conway et al. | |
| 4,882,777 A | 11/1989 | Narula | |
| 4,883,058 A | 11/1989 | Riuz | |
| 4,886,506 A | 12/1989 | Lovgren et al. | |
| 4,896,670 A | 1/1990 | Crittenden | |
| 4,898,577 A | 2/1990 | Badger et al. | |
| 4,898,591 A | 2/1990 | Jang et al. | |
| 4,909,787 A | 3/1990 | Danforth | |
| 4,917,103 A | 4/1990 | Gambale et al. | |
| 4,922,923 A | 5/1990 | Gambale et al. | |
| 4,925,445 A | 5/1990 | Sakamoto et al. | |
| 4,935,004 A | 6/1990 | Cruz | |
| 4,935,017 A | 6/1990 | Sylvanowicz | |
| 4,950,228 A | 8/1990 | Knapp, Jr. et al. | |
| 4,973,306 A | 11/1990 | Ruiz | |
| 4,976,691 A | 12/1990 | Sahota | |
| 4,981,477 A | 1/1991 | Schon et al. | |
| 4,983,166 A | 1/1991 | Yamawaki | |
| 4,994,032 A | 2/1991 | Sugiyama et al. | |
| 5,000,743 A | 3/1991 | Patel | |
| 5,016,640 A | 5/1991 | Ruiz | |
| 5,031,636 A | 7/1991 | Gambale et al. | |
| 5,035,686 A | 7/1991 | Crittenden et al. | |
| 5,040,548 A | 8/1991 | Yock | |
| 5,044,369 A | 9/1991 | Sahota | |
| 5,045,072 A | 9/1991 | Castillo et al. | |
| 5,058,595 A | 10/1991 | Kern | |
| 5,059,197 A | 10/1991 | Uri et al. | |
| 5,061,273 A | 10/1991 | Yock | |
| 5,098,412 A | 3/1992 | Shiu | |
| 5,122,125 A | 6/1992 | Deuss | |
| 5,135,535 A | 8/1992 | Kramer | |
| 5,154,725 A | 10/1992 | Leopold | |
| 5,163,921 A | 11/1992 | Feiring | |
| 5,195,971 A | 3/1993 | Sirhan | |
| 5,195,990 A | 3/1993 | Weldon | |
| 5,203,776 A | 4/1993 | Durfee | |
| 5,215,540 A | 6/1993 | Anderhub | |
| 5,232,445 A | 8/1993 | Bonzel | |
| 5,279,562 A | 1/1994 | Sirhan et al. | |
| 5,299,574 A * | 4/1994 | Bower | 600/435 |
| 5,306,263 A * | 4/1994 | Voda | 604/532 |
| 5,401,258 A * | 3/1995 | Voda | 604/532 |
| 5,445,625 A * | 8/1995 | Voda | 604/532 |
| 5,462,527 A * | 10/1995 | Stevens-Wright et al. | 604/528 |
| 5,846,229 A * | 12/1998 | Berg | 604/528 |
| 5,868,700 A * | 2/1999 | Voda | 604/510 |
| 5,876,385 A * | 3/1999 | Ikari et al. | 604/523 |
| 5,885,259 A * | 3/1999 | Berg | 604/532 |
| 5,902,287 A * | 5/1999 | Martin | 604/532 |
| 5,916,209 A * | 6/1999 | Mick | 604/523 |
| 5,941,872 A * | 8/1999 | Berg | 604/532 |
| 5,971,974 A * | 10/1999 | Keisz | 604/523 |
| 5,980,502 A * | 11/1999 | Berg | 604/508 |
| 6,083,213 A * | 7/2000 | Voda | 604/500 |
| 6,110,163 A * | 8/2000 | Voda | 604/523 |
| 6,120,495 A * | 9/2000 | Voda | 604/523 |
| 6,132,417 A * | 10/2000 | Kiesz | 604/523 |
| 6,355,026 B1 * | 3/2002 | Mick | 604/523 |
| 6,558,368 B1 * | 5/2003 | Voda | 604/532 |
| 6,595,983 B2 * | 7/2003 | Voda | 604/530 |
| 6,638,268 B2 * | 10/2003 | Niazi | 604/528 |
| 2002/0103474 A1 * | 8/2002 | Voda | 604/530 |

FOREIGN PATENT DOCUMENTS

| | | |
|---|---|---|
| EP | 0 256 478 A1 | 2/1988 |
| EP | 0 277 366 A1 | 8/1988 |
| EP | 0 323 738 A2 | 7/1989 |
| WO | WO 92/12754 | 8/1992 |

OTHER PUBLICATIONS

Williams Right WR Angiographic Catheter, Boston Scientific SciMed, Inc., Maple Grove, Minnesota (undated but admitted to be prior art).

Mallinckrodt Medical, Inc., "Diagnostic Catheters" Brochure (1990) (1 page).

USCI "KIFA Products" Brochure, pp. 1-12, Jun. 1974.

USCI "KIFA Catheterization Equipment" Brochure, pp. 1-7 (1967).

USCI "USCI® Grüntzig Dilaca™ Coronary Dilatation Equipment" Brochure, C. R. Bard, Inc. (1990) (4 pages).

USCI "Positrol II® and Nycore™ Cardiovascular Catheters" Brochure, pp. 1-21.

Arani, "A New Catheter for Angioplasty of the Right Coronary Artery and Aorto-Coronary Bypass Grafts", *Catheterization and Cardiovascular Diagnosis* 11:647-653 (1985).

*PTCA in Perspective,* USCI/Technical Perspective [Block, P.C. et al., USCI Division, C. R. Bard, Inc., Billerica, Mass., pp. 23-42 (1986)].

King, S. B., III, Douglas, J. S., Jr. and Gruentzig, A. R.: *Coronary Arteriography and Angioplasty,* McGraw-Hill, New York, Chapter 17, "Percutaneous Transluminal Coronary Angioplasty," pp. 433-451 (1985).

Amplatz, K., Formanek, G., Stanger, P. and Wilson, W.: "Mechanics of Selective Coronary Artery Catheterization via Femoral Approach," *Radiology 89*: 1040-1047, Dec. 1967.

Judkins, M. P., "Percutaneous Transfemoral Selective Coronary Arteriography," *Radiologic Clinics of North America,* vol. VI, No. 3, pp. 467-492, Dec. 1968.

Carr, M. L., "The Use of the Guiding Catheter in Coronary Angioplasty: The Technique of Manipulating Catheters to Obtain the Necessary Power to Cross Tight Coronary Stenoses," *Catheterization and Cardiovascular Diagnosis* 12:189-197 (1986).

King, S. B., III, and Douglas J. S., Jr.: *Coronary Arteriography and Angioplasty,* McGraw-Hill, New York, Chapter 7, Judkins, M. P. and Judkins, E., "Coronary Arteriography and Left Ventriculography: Judkins Technique," pp. 182-238 (1985).

Medi-Tech® Boston Scientific Corporation "Imager Angiographic Catheters" Brochure, Oct. 1990 (4 pages).

Bourassa, M. G., Lesperance, J. and Campeau, L.: "Selective Coronary Arteriography by the Percutaneous Femoral Artery Approach," Montreal Heart Institute, Montreal, Quebec, Canada, vol. 107, No. 2, pp. 377-383, Oct. 1969.

USCI Video Tape, "Select Curve Guiding Catheter: Cannulating the Right Coronary Artery" (1988).

Voda, Jan K., "Angled Tip of the Steerable Guidewire and Its Usefulness in Percutaneous Transluminal Coronary Angioplasty," *Catheterization and Cardiovascular Diagnosis* 13:204-210 (1987).

Bourassa "Cardiovascular Catheters Sterile" brochure, 4 pages, Jun. 1972.

El Gamal et al., Improved Success Rate of Percutaneous Transluminal Graft and Coronary Angioplasty with the El Gamal Guiding Catheter, Catherization and Cardiovascular Diagnosis, 11:89-96 (1985).

SciMed Life Systems, Inc. Guiding Catheter Training, 1990.

USCI Block Right Coronary Guiding Catheter, 2 pages, 1989.

USCI Video Tape ("Select Curve Guiding Catheter: Cannulating the Right Coronary Artery") transcript and selected figures, 1988.

Wilson et al., Biplane Selective Coronary Arteriography Via Percutaneous Transfemoral Approach, presented at the Sixty-Seventh Annual Meeting of the American Roentgen Ray Society, San Francisco, California, Sep. 27-30, 1966.

\* cited by examiner

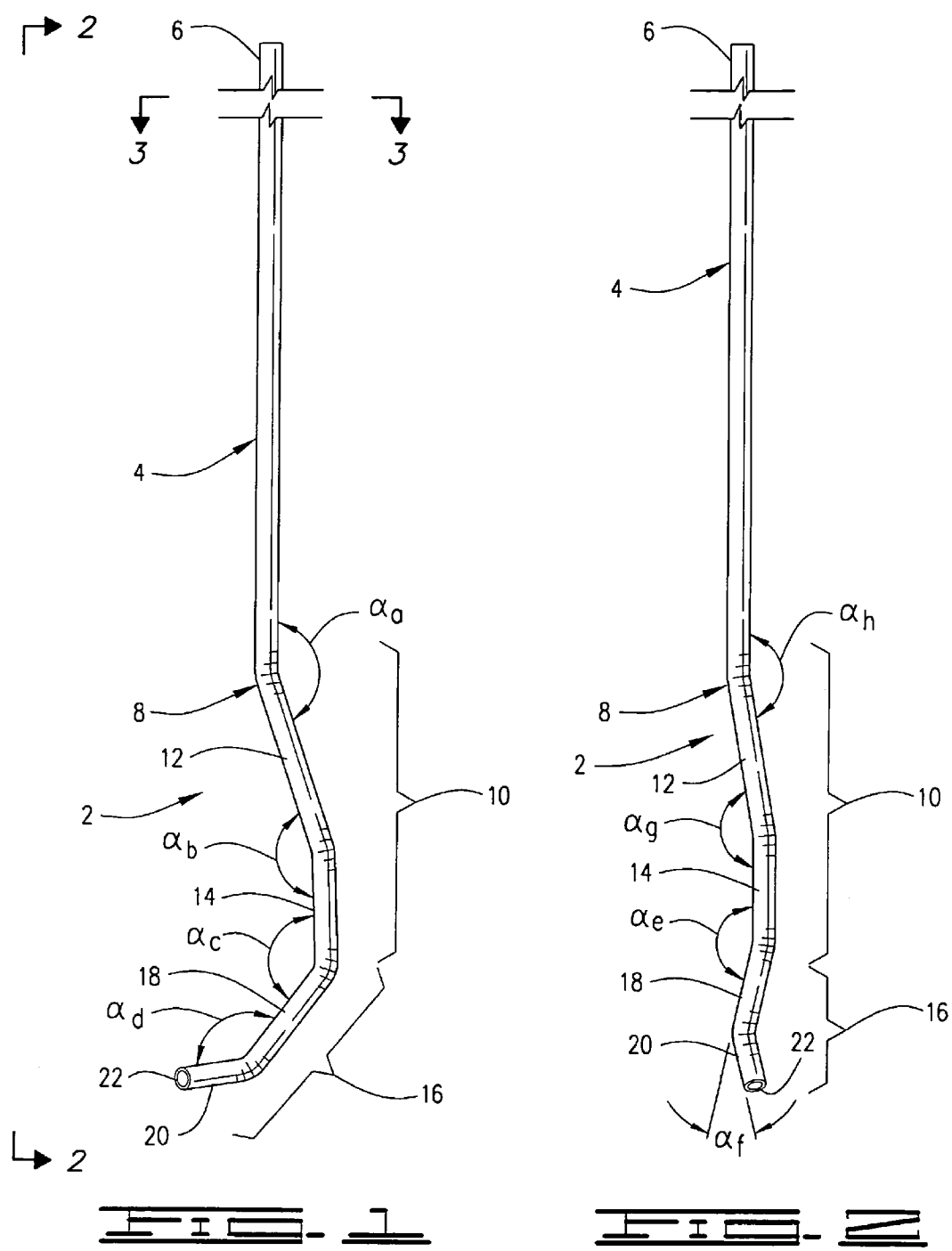

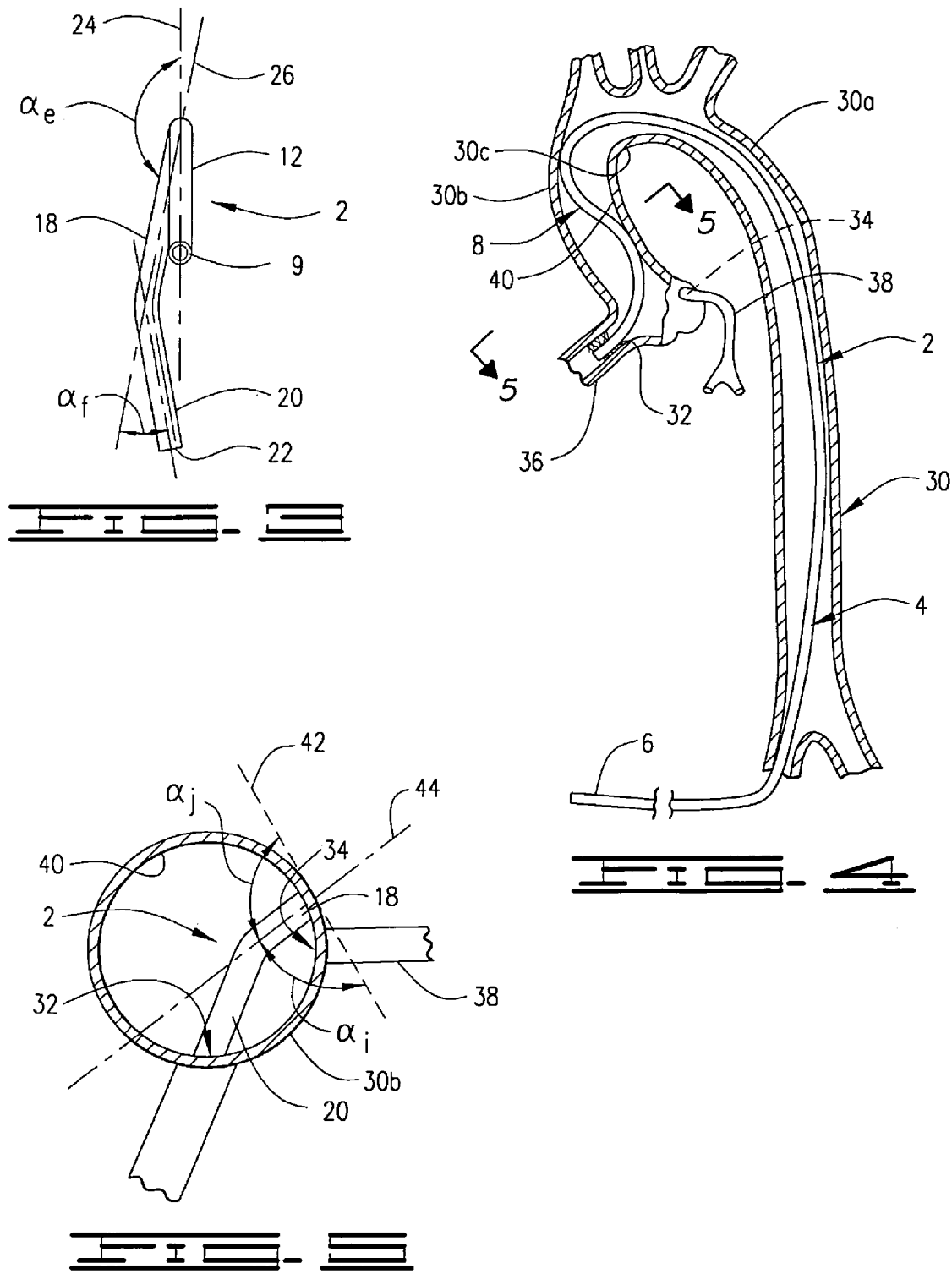

STEERABLE CATHETER FOR RIGHT CORONARY ARTERY

BACKGROUND OF THE INVENTION

This invention relates generally to catheters for coronary arteries and more particularly to a steerable catheter that has a distal segment to abut an inside surface of an ascending aorta and that also has a three dimensional distal portion to facilitate entry of a distal tip into the ostium of a right coronary artery extending from the ascending aorta such that the catheter is adequately supported for subsequent procedures.

The use of catheters in diagnosing and treating vessels in a human body is well known. One particular known therapeutic use of catheters is in performing percutaneous transluminal coronary angioplasty (PTCA). One technique for performing PTCA in a right coronary artery includes inserting a guide catheter into a femoral artery and advancing the guide catheter such that its distal tip moves through that artery, up the descending aorta, and ultimately into the ostium of the right coronary artery. A balloon catheter may then be pushed through the guide catheter into the right coronary artery to perform medical procedures in known manner. As an example of a diagnostic use, a diagnostic catheter can be similarly placed and then used to conduct a radiopaque dye injected in known manner. The main difference between a guide catheter and a diagnostic catheter is that the lumen is typically larger in a guide catheter to accommodate various tools and instruments that are pushed through the lumen.

Catheter terminology has not be consistently used or adopted by the medical profession or by medical publications. Accordingly, for definitional purposes herein, catheters for the right coronary artery can be divided into two functional categories: the "completely preformed catheter" and the "steerable catheter". Both types have a preformed tip designed to be positioned in the ostium of the right coronary artery. The completely preformed catheter, known by some as a non-torqueable catheter, is designed such that the preformed tip can be positioned in the ostium of the right coronary artery simply by advancing the catheter to the proper level, without manipulating or torquing (twisting) the catheter. Completely preformed catheters generally require a lower degree of skill to position the tip in the ostium of the right coronary artery; however, they do not always work well for all patients due to different morphologies among patients.

The second type of catheter for the right coronary artery is the "steerable catheter". A steerable catheter, known by some as a partially preformed catheter or a torquable catheter, can be torqued (twisted) to steer the catheter to the desired location. The proximal end of the catheter is torqued, typically in a clockwise direction, which causes the distal end of the catheter to also twist and be steered into the ostium of the right coronary artery. Steerable catheters require a greater degree of skill, but work with a greater variety of morphologies. Steerable catheters (and fully preformed catheters) can be used for both therapeutic and diagnostic purposes and thus include both guide and diagnostic catheters. In other words, "steerable catheter" as used herein includes the subclasses of both guide and diagnostic catheters.

There are no known three-dimensioned steerable guide catheters in the marketplace. The VR (Voda Right) catheter available from Scimed Life Systems, Inc. is three-dimensional and is a guide-type catheter, but it is not steerable. The Williams catheter also available from Scimed Life Systems, Inc. is a three-dimensional steerable catheter, but it is a diagnostic catheter and not a guide catheter.

Thus, there are known types of catheters designed for the right coronary artery. However, there remains the need for a new type of steerable catheter that can be readily used with different right coronary artery morphologies found in patients. There is also a need for a steerable catheter, especially of the guide type, that can be better controlled and that has a distal end that is better supported and more stable when the tip is positioned in the ostium of the right coronary artery so the forces exerted by pushing tools and instruments through the lumen of the catheter do not cause the tip to move or become dislodged from the ostium of the right coronary artery. There is the particular need for a steerable catheter which has a preformed three-dimensional distal end portion having a tip and shaped such that the tip readily enters the ostium of the right coronary artery upon the placement of the catheter or when suitable torque is applied to the proximal end of the catheter and such that the distal end portion is adequately supported for subsequent procedures. Such need is intended to be satisfied pursuant to the disclosure in my U.S. Pat. No. 6,595,983; however, an improvement on my prior invention has been invented as described below.

SUMMARY OF THE INVENTION

The present invention meets the aforementioned needs by providing a novel and improved catheter for a right coronary artery and especially a three dimensional steerable catheter to selectively engage the ostium of a right coronary artery in a patient. The catheter of the present invention has a distal tip that can be readily placed in the ostia of right coronary arteries across a range of morphologies for such arteries and that is adequately supported when properly positioned. The structure of the catheter is such that it allows a relatively long, atraumatic tip to be used which provides for easier, less traumatic use of the catheter.

Such a steerable catheter as defined by the present invention to engage the ostium of a right coronary artery in a patient comprises a proximal shaft having a proximal end to receive manipulation by a user outside a patient in whom the catheter is used, wherein the proximal shaft transmits torque applied at the proximal end. This catheter further comprises a distal shaft extending from the proximal shaft opposite the proximal end of the proximal shaft such that the distal shaft is responsive to torque transmitted by the proximal shaft. The distal shaft includes a preformed support section including: a transition segment extending from the proximal shaft; and an abutment segment extending from the transition segment such that the abutment segment abuts an interior surface of the ascending aorta of the patient when the catheter is in place within the patient. The distal shaft also includes a preformed ostium entry section extending from the support section. It includes a first segment, extending from the abutment segment, and a second segment, extending from the first segment. In at least a natural state of the catheter outside the patient with the support section of the catheter in a sagital plane relative to the patient, the first segment of a preferred embodiment lies in that sagital plane or to the patient's right of that sagital plane when the first segment extends to the patient's anterior from the preformed support section, and the second segment extends back toward such sagital plane.

A catheter for a right coronary artery in accordance with the present invention can also be defined as comprising: a proximal shaft having a proximal end to receive manipulation by a user outside a patient in whom the catheter is used; and a distal shaft extending from the proximal shaft opposite the proximal end of the proximal shaft. The distal shaft includes a preformed support section to abut a posterior interior surface of the ascending aorta of the patient. This support section includes: a transition segment connected to the proximal shaft at a first bend initially forming an included angle of between 135° and 175°, wherein the transition segment is initially substantially linear; and an abutment segment connected to the transition segment at a second bend initially forming an included angle of between 135° and 175°, wherein the abutment segment is initially substantially linear. The distal shaft also includes a preformed ostium entry section extending from the preformed support section. The preformed ostium entry section includes: a first segment connected to the abutment segment at a third bend initially forming an included angle of between 80° and 170°, wherein the first segment is initially substantially linear; a second segment connected to the first segment at a fourth bend initially forming an included angle of between 90° and 175°, wherein the second segment is initially substantially linear; and wherein the first and second segments are initially offset in different directions from an imaginary plane including at least the abutment segment of the preformed support section. In a particular implementation, the first segment is disposed at an initial angle of 130° to 180° relative to one such imaginary plane; and the second segment is disposed at an initial angle of 0° to 90° from a plane defined by the first segment and the abutment segment of the preformed support section. In a more specific implementation, the transition segment has a length between 20 millimeters and 80 millimeters, the abutment segment has a length between 5 millimeters and 40 millimeters, the first segment has a length between 5 millimeters and 55 millimeters, and the second segment has a length between 5 millimeters and 55 millimeters. The second segment terminates at a distal tip which enters the ostium of a right coronary artery when the catheter is properly placed in the patient. There may be another bend between the transition segment and the proximal shaft of between 140° and 180° and another bend between the abutment segment and the transition segment of between 140° and 180°. The transition segment can be twisted relative to the proximal shaft.

A three dimensional steerable catheter to engage the ostium of a right coronary artery of a patient can also be defined as comprising a proximal shaft and a distal shaft extending from the proximal shaft. The distal shaft includes: a preformed support section having a transition segment extending from the proximal shaft; an abutment segment extending from the transition segment; and a preformed ostium entry section extending from the support section. The ostium entry section includes a first segment, extending from the abutment segment, and a second segment, extending from the first segment. The second segment terminates in a distal tip. When the proximal shaft is torqued clockwise to engage the distal tip into the ostium of the right coronary artery, the distal tip follows a plane that includes the abutment section and a point of connection between the first segment and the second segment.

A three dimensional steerable catheter to selectively engage the ostium of a right coronary artery of a patient can also be defined as comprising a proximal shaft having a proximal end to receive manipulation by a user outside the patient in whom the catheter is used, wherein the proximal shaft transmits torque applied at the proximal end. A distal shaft extends from the proximal shaft opposite the proximal end of the proximal shaft such that the distal shaft is responsive to torque transmitted by the proximal shaft. The distal shaft includes a preformed support section having a transition segment extending from the proximal shaft and an abutment segment extending from the transition segment. The preformed support section also includes a preformed ostium entry section extending from the support section and including a first segment extending from the abutment segment. The abutment segment abuts an interior surface of the patient's ascending aorta in a plane formed by a tangent of an axis of the first segment when the catheter is positioned within the ostium of the right coronary artery.

A three dimensional steerable catheter to engage the ostium of a right coronary artery of a patient can also be defined as comprising a proximal shaft and a distal shaft extending from the proximal shaft. The distal shaft includes: a preformed support section having a transition segment extending from the proximal shaft and an abutment segment extending from the transition segment; and a preformed ostium entry section extending from the support section and having a first segment, extending from the abutment segment, and a second segment, extending from the first segment. The second segment terminates in a distal tip such that when the distal tip is positioned in the ostium of the right coronary artery the first segment and the second segment lie anterior to the support section.

A three dimensional steerable catheter to selectively engage the ostium of a right coronary artery of a patient can also be defined as comprising an abutment segment, a first segment extending from the abutment segment and a second segment extending from the first segment and terminating in a distal tip. When the distal tip is positioned within the ostium of the right coronary artery of the patient, the abutment segment abuts an interior surface of the patient's ascending aorta in a plane formed by a tangent of an axis of the first segment and the second segment is coaxial to an axis of the patient's right coronary artery.

Therefore, from the foregoing, it is a general object of the present invention to provide a novel and improved catheter for a right coronary artery and especially a three dimensional steerable catheter to selectively engage the ostium of a right coronary artery in a patient. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 1 is a side or lateral view of a preferred embodiment of the present invention.

FIG. 2 is an anterior-posterior view of the preferred embodiment as taken along line 2-2 shown in FIG. 1.

FIG. 3 is a view of the preferred embodiment as taken along line 3-3 shown in FIG. 1.

FIG. 4 schematically illustrates aortic and left and right coronary arterial structures for a patient in which a catheter as shown in FIGS. 1-3 is placed.

FIG. 5 is a view along line 5-5 in FIG. 4.

DETAILED DESCRIPTION OF THE INVENTION

A catheter 2 for a right coronary artery in accordance with the present invention is illustrated in FIGS. 1-3. The catheter 2 comprises a proximal shaft 4 having a proximal end 6 to receive manipulation by a user (not shown) outside a patient in whom the catheter 2 is used. The catheter 2 further comprises a distal shaft 8 extending from the proximal shaft 4 opposite the proximal end 6. At least one lumen 9 extends through the shafts 4, 8 to permit passage of other devices (e.g., a balloon catheter when catheter 2 is a guide catheter) or substances (e.g., a radiopaque dye when the catheter is a diagnostic catheter).

The distal shaft 8 includes a preformed support section 10 which both longitudinally and laterally supports a more distal portion of the catheter terminating in a tip 22. A transition segment 12, connected to the proximal shaft 4 at a first bend or curve initially forming an included angle $\alpha_a$ of between 135° and 175° or thereabouts, provides longitudinal and lateral support for the distal tip 22 so as to provide an offset from the axis of the proximal shaft 4 whereby the tip 22 section can be relatively long. Stated another way, the transition segment 12 enables a longer distal tip to function as a shorter tip in passing through the body vessels and into the ostium of the right coronary artery, while maintaining the more gentle curve of a long tip when in the ostium of the right coronary artery, thereby facilitating the ability to move other equipment or substances through the bend and into the artery. Length in the tip compensates for the offset used to enable lateral support, and length facilitates more gradual angular transitions. The transition segment 12 preferably is initially substantially linear and has a length between 20 millimeters and 80 millimeters (or thereabouts) in the preferred embodiment. "Natural state" or "initially" as used here and elsewhere, including the claims, with regard to angularity or linearity pertains to a relaxed state of the catheter or its elements after the catheter has been manufactured but before it has been placed in use in a patient. "About" or "thereabouts" as used here and elsewhere, including the claims, with regard to angularity or linearity encompasses small deviations from the stated range endpoints. Even an absolute range encompasses deviations due to engineering tolerances. Furthermore, references to angles, bends, curves, points of connection and the like in this description and in the claims are not to be taken as excluding various transitions from one segment to another; that is, these may be linearly sharp or distinct transitions, but may be, and preferably are, radiused or smooth curvilinear transitions.

The present invention is for use in a human body or a patient, and these terms are used synonymously herein. Directional references used herein (e.g., anterior, posterior, left, right) and in the claims are relative to the patient in accordance with medical vernacular, except where these direction references are indicated as relative to something other than the patient (e.g., relative to another portion of the catheter). For example, patient's left means towards to patient's left hand.

The preformed support section 10 also comprises an abutment segment 14 connected to the transition segment 12 at a second bend or curve initially forming an included angle $\alpha_b$ of between 135° and 175° or thereabouts. In a preferred embodiment, $\alpha_a$ and $\alpha_b$ are substantially the same angle such that proximal shaft 4 is substantially parallel to abutment segment 14. The abutment segment 14 preferably is initially substantially linear and has a length between 5 millimeters and 40 millimeters or thereabouts in the preferred embodiment. The abutment segment 14 provides support relative to the aortic wall. That is, the segment 14 abuts posteriorly on the interior wall of the ascending aorta when positioned as shown in FIGS. 4 and 5, which provides resistance against the distal tip 22 disengaging the ostium of the right coronary artery once the catheter is properly positioned. This support is provided along the length of the segment 14 rather than at only a small point contact, whereby more stable support is provided by the segment 14.

The distal shaft 8 also includes a preformed ostium entry section 16 extending from the preformed support section 10 and terminating at the tip 22. The preformed ostium entry section 16 includes a first segment 18 connected to the abutment segment 14 at a third bend or curve initially forming an included angle $\alpha_c$ of between 80° and 170° or thereabouts. The first segment 18 preferably is initially substantially linear and has a length between 5 millimeters and 55 millimeters or thereabouts in the preferred embodiment.

The preformed ostium entry section 16 further has a second segment 20 connected to the first segment 18 at a fourth bend or curve initially forming an included angle $\alpha_d$ of between 90° and 175° or thereabouts. The second segment terminates at the distal tip 22, preferably a soft, atraumatic tip to reduce damage during positioning and torquing. The second segment 20 preferably is initially substantially linear and has a length between 5 millimeters and 55 millimeters or thereabouts (with the tip 22 being about 5 millimeters long) in the preferred embodiment.

The first and second segments 18, 20 that direct tip 22 into the ostium of the right coronary artery are initially offset from an imaginary plane 24 containing the transition and abutment segments 12, 14 of the preformed support section 10 in the orientation shown in FIG. 3, thereby making the catheter 2 into what is referred to as a three-dimensional catheter. As used herein and in the claims, "three-dimensional" means, in at least a natural state of the catheter outside the patient, a shape or configuration outside more than a single principal plane of the axis of the lumen 9 of the catheter 2). In other words, the lateral view shown in FIG. 1 illustrates two dimensions, the first being the length of catheter 2 and the second being the angles shown in FIG. 1 (namely, $\alpha_a$, $\alpha_b$, $\alpha_c$ and $\alpha_d$). The third dimension is illustrated in FIG. 2, which shows angles $\alpha_e$, $\alpha_f$, $\alpha_g$ and $\alpha_h$.

In a presently preferred embodiment, in at least a natural state of this particular configuration outside the patient, the segment 18 is preformed to lie only to the right of or coplanar with the plane 24 when the plane 24 is in front of and parallel to a patient's sagital plane when the preformed ostium entry section extends to the patient's anterior from the preformed support section (this would place the patient behind and facing toward catheter 2 in FIG. 2, or to the right of and facing toward catheter 2 in FIG. 1, or above and facing toward catheter 2 in FIG. 3). In a presently preferred embodiment, once properly placed in the body, the segment 18 extends generally to the patient's anterior and to the patient's right or clockwise from a plane through the aorta parallel to the sagittal (i.e., midsagittal) plane. Referencing to the catheter 2 itself, in a particular implementation, the first segment 18 is disposed at an initial angle $\alpha_e$ of 130° to 180° or thereabouts relative to the plane 24 of the support section 10. While preferably less than 180°, $\alpha_e$ may be equivalent to 180° such that abutment section 14 and first segment 18 appear to be linear in the anterior-posterior view shown in FIG. 2. The second segment 20, on the other hand, extends in a different direction back toward the plane 24, including to the extent of intersecting it. In a particular implementation, the second segment 20 is disposed at an initial angle $\alpha_f$ of 0° to 90° or thereabouts from an imaginary plane 26 (FIG. 3) defined by the first segment 18 and the abutment segment 14. The planes 24, 26 are both perpendicular to an imaginary reference plane, such as the plane of the sheet containing FIG. 3.

Although the foregoing description of the orientation of segments 18, 20 refers to plane 24 as defined by segments 12, 14 as illustrated, it is noted that segments 12 and 14 need not actually lie in this same plane in all embodiments of the present invention. In general, the abutment segment 14 can be at an angle $\alpha_g$ (FIG. 2) of between 140° and 180° or thereabouts relative to the axial line of the transition segment 12 or the plane 24. Similarly, the transition segment 12 can be bent or curved relative to the proximal shaft 4 or the plane 24, such as at an angle $\alpha_h$ (FIG. 2) of between 140° and 180° (or more)

or thereabouts. Thus, these segments can be offset at one or two angles or curves (which can also be achieved as rotations) relative to one of the stated references. Furthermore, the distal portion can be twisted relative to the proximal portion. That is, the transition segment 12 (and thus the other distal portions extending from it) can be twisted (for example, from about 5° to 90°) relative to the proximal shaft 4. This twisting may accommodate the placement of tip 22 into ostium 32 of right coronary artery 36 in a variety of morphologies found in patients.

The catheter of the present invention can be made of known materials and with known techniques. The material or materials of construction may be the same throughout the catheter, or different materials may be used. A typical material is a known type of plastic used in other catheters, and it can be of a type which itself provides sufficient stiffness to have a desired torque-transmitting capability; however, other constructions can be used, a non-limiting example of which is to incorporate a metallic wire or braid in or with the plastic tubing of the catheter body to provide or enhance the torque-transmitting characteristic of the catheter. Preferably the material of construction prevents or reduces trauma as the catheter is moved through the body (this is especially desirable for the tip 22 which preferably is defined by a thin wall made of a very soft material as known in the art). One or more particular combinations of angles and lengths from the aforementioned ranges are selected for manufacturing specific catheters as are suitable for use in a human.

Part of a typical human cardiovascular system is schematically shown in the side or lateral view of FIG. 4 and the indicated sectional view of FIG. 5. This system includes an aorta 30 comprised of a descending aorta 30a, an ascending aorta 30b, and an aortic arch 30c which extends from the descending aorta 30a to the ascending aorta 30b over a curve of approximately 180°. The ascending aorta 30b branches through a right ostium 32 and a left ostium 34 into a right coronary artery 36 and a left coronary artery 38, respectively. The left and right coronary arteries 38 and 36 are typically separated by an angle of approximately 120°.

Also represented in FIGS. 4 and 5 is the catheter 2 placed for effective use in a patient. Placement of the catheter 2 as shown in FIGS. 4 and 5 usually occurs through a femoral artery using a technique applied to achieve the illustrated positioning of the catheter 2. This positioning includes having the abutment segment 14 of the preformed support section 10 abut an interior surface of the ascending aorta 30b of the patient substantially opposite the ostium 32, which typically is a posterior interior surface 40. Entry of the distal tip 22 into the ostium 32 is obtained by applying torque to the proximal end 6 and transmitting the torque through the proximal shaft 4 and the distal shaft 8. More specifically, the catheter 2 is advanced in conventional manner until the distal tip 22 is slightly above the ostium 32 of the right coronary artery 36. As the proximal end 6 is torqued clockwise, the shafts 4 and 8 rotate in response, and the distal tip 22 rotates and lowers into engagement with the ostium 32. In a preferred embodiment abutment segment 14 is positioned at least about 5 millimeters above the level of the ostium 32 when distal tip 22 is positioned within the ostium 32. Also, in a preferred embodiment, first segment 18 and second segment 20 lie anterior to support section 10 when distal tip 22 is positioned within the ostium 32. Such a geometric configuration allows distal tip 22 to be positioned deeper into the coronary artery 36 (i.e., effectively lengthens catheter 2) such that distal tip 22 is more secure and less likely to become dislodged from the coronary artery 36 when pushing tools or other substances through the lumen 9 of the catheter. Engagement with the ostium 32 is secured by the abutment segment 14 engaging the aortic wall, and ease of equipment or substance transmission through the lumen 9 of the catheter 2 is facilitated by the relatively long distal tip 22 as offset by the transition segment 12.

The three dimensional configuration of the present invention allows distal tip 22 to be inserted into the ostia of right coronary arteries across a range of morphologies. This is accomplished, in part, because distal tip 22 and second segment 20 are coaxial with the axis of the right coronary artery when properly positioned. This coaxial arrangement reduces trauma to the right coronary artery when the catheter is positioned in the right coronary artery and allows distal tip 22 to be inserted deeper into the right coronary artery. Moreover, angle $\alpha_f$ creates a deviation of the second segment 20 to the patient's left (when tip 22 is directed anteriorly of a patient). This deviation to the left allows distal tip 22 to follow (rather than lead if there was a deviation to the right) when catheter 2 is torqued in the customary clockwise direction. That is, distal tip 22 follows an imaginary plane that includes abutment segment 14 and a point of connection between first and second segments 18, 20 when proximal end 6 is torqued clockwise. As previously indicated, the point of connection between first and second segments 18, 20 may be a distinct transition or a radiused or smooth curvilinear transition. Having the distal tip 22 follow may minimize gouging and damage caused by rotating and may reduce the amount of torque (force) necessary to rotate catheter 2 (even though catheter 2 must be twisted a greater number of degrees as compared to a deviation to the right.).

The three dimensional configuration of the present invention also allows for enhanced stability and support when the distal tip 22 is positioned in the ostium 32 of a right coronary artery 36. More specifically, abutment section 14 abuts the interior surface of the ascending aorta 30b in a plane defined by the tangent at the interior surface of the ascending aorta 30b, where tangent 42 is substantially perpendicular to axis 44 of first segment 18. Thus, referring to FIG. 5, $\alpha_i$ and $\alpha_j$ are in the range of about 60-120°, or more preferably in the range of about 70°-110° but are most preferably 90°. This substantially perpendicular alignment, especially when combined with the feature of the second segment 20 being coaxial with the axis of the right coronary artery as previously described herein, provides support and stability when tip 22 is positioned in the ostium 32 so the forces exerted by pushing tools and instruments through the lumen 9 of the catheter 2 do not cause the distal tip 22 to move or become dislodged from the ostium 32 of the right coronary artery 36.

Accordingly, the present invention provides a preformed, steerable catheter, particularly a preformed, steerable guide or diagnostic catheter, for a right coronary artery.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. A three dimensional steerable catheter to engage the ostium of a right coronary artery of a patient comprising:
   a proximal shaft having a long axis; and
   a distal shaft extending from the proximal shaft, the distal shaft including:
   a preformed support section including a transition segment extending from the proximal shaft and an abutment segment extending from the transition segment, wherein a portion of the proximal shaft adjacent to the distal shaft, the transition segment and the abutment segment generally define a first plane and the portion of the proximal shaft and the abutment segment are generally parallel; and a preformed ostium entry section comprising a first ostium segment extending from the abutment segment;

a second ostium segment extending from the first ostium segment at a point of connection; and a distal tip of the second ostium segment, wherein the abutment segment and the point of connection between the first ostium segment and the second ostium segment define a second plane not coincident with the first plane, wherein the three dimensional steerable catheter has a first configuration and a second configuration, which configurations differ in the angle between the first plane and the second plane, further wherein when the proximal shaft is rotated clockwise about the long axis and the abutment segment rests at least in part against an obstruction, the configuration of the three dimensional steerable catheter changes from the first configuration to the second configuration and the distal tip follows the second plane as it rotates in response to rotation of the proximal shaft.

2. The catheter of claim 1 wherein the abutment segment abuts an interior surface of the patient's ascending aorta in a plane formed by a tangent of an axis of the first segment when the distal tip is positioned within the ostium of the right coronary artery.

3. The catheter of claim 1 wherein the second segment is coaxial to an axis of the right coronary artery when the distal tip is positioned within the ostium of the right coronary artery.

4. The catheter of claim 1 wherein the transition segment is twisted relative to the proximal shaft.

5. The catheter of claim 1 wherein the abutment segment is positioned at least about 5 millimeters above the level of the ostium of the right coronary artery when the distal tip is positioned within the ostium of the right coronary artery.

6. The catheter of claim 1 wherein in at least a natural state of the catheter outside the patient with the support section extending distally in a vertical plane, the first segment lies in or to the right of such vertical plane of the support section when the first segment extends upwardly from the preformed support section, and the second segment extends back toward such vertical plane.

7. The catheter of claim 6 wherein:
the first segment is connected to the support section such that the first segment is initially disposed at a first angle from the support section and at a second angle from the plane of the support section;
the second segment is connected to the first segment such that the second segment is initially disposed at a third angle from the first segment and at a fourth angle from a plane defined by the first segment and at least a portion of the support section;
the first angle is within the range of about 80° to about 170°;
the second angle is within the range of about 130° to about 180°;
the third angle is within the range of about 90° to about 175°; and
the fourth angle is within the range of about 0° to about 90°.

8. The catheter of claim 7 wherein the transition segment is disposed at one initial angle with the proximal shaft of between about 135° and about 175° and at one initial angle with the abutment segment of between about 135° and about 175° and wherein the transition segment is disposed at another initial angle with the proximal shaft of between about 140° and about 180° and at another initial angle with the abutment segment of between about 140° and about 180°.

9. The catheter of claim 8 wherein:
the transition segment has a length between about 20 millimeters and about 80 millimeters;
the abutment segment has a length between about 5 millimeters and about 40 millimeters;
the first segment has a length between about 5 millimeters and about 55 millimeters; and
the second segment has a length between about 5 millimeters and about 55 millimeters.

10. The catheter of claim 1 wherein:
the first segment is connected to the support section such that the first segment is initially disposed at a first angle from the support section and at a second angle from the plane of the support section;
the second segment is connected to the first segment such that the second segment is initially disposed at a third angle from the first segment and at a fourth angle from a plane defined by the first segment and at least a portion of the support section;
the first angle is within the range of about 80° to about 170°;
the second angle is within the range of about 130° to about 180°;
the third angle is within the range of about 90° to about 175°; and
the fourth angle is within the range of about 0° to about 90°.

11. The catheter of claim 1 wherein the transition segment is disposed at one initial angle with the proximal shaft of between about 135° and about 175° and at one initial angle with the abutment segment of between about 135° and about 175° and wherein the transition segment is disposed at another initial angle with the proximal shaft of between about 140° and about 180° and at another initial angle with the abutment segment of between about 140° and about 180°.

12. The catheter of claim 1 wherein:
the transition segment has a length between about 20 millimeters and about 80 millimeters;
the abutment segment has a length between about 5 millimeters and about 40 millimeters;
the first segment has a length between about 5 millimeters and about 55 millimeters; and
the second segment has a length between about 5 millimeters and about 55 millimeters.

* * * * *